(12) United States Patent
Kang-Budialam et al.

(10) Patent No.: US 10,874,507 B2
(45) Date of Patent: Dec. 29, 2020

(54) SURGICAL INTRODUCER

(71) Applicant: Northwood Medical Innovation Limited, London (GB)

(72) Inventors: Norbert Venantius Kang-Budialam, London (GB); Marie-Claire Haines, London (GB)

(73) Assignee: Northwood Medical Innovation Limited, London (GB)

( * ) Notice: Subject to any disclaimer, the term of this patent is extended or adjusted under 35 U.S.C. 154(b) by 69 days.

(21) Appl. No.: 15/129,369

(22) PCT Filed: Feb. 10, 2015

(86) PCT No.: PCT/GB2015/050356
§ 371 (c)(1),
(2) Date: Sep. 26, 2016

(87) PCT Pub. No.: WO2015/145102
PCT Pub. Date: Oct. 1, 2015

(65) Prior Publication Data
US 2017/0100235 A1    Apr. 13, 2017

(30) Foreign Application Priority Data

Mar. 26, 2014  (GB) .................................. 1405414.2

(51) Int. Cl.
*A61F 2/18*     (2006.01)
*A61F 2/00*     (2006.01)
(Continued)

(52) U.S. Cl.
CPC ............ *A61F 2/18* (2013.01); *A61B 17/3468* (2013.01); *A61F 2/0059* (2013.01);
(Continued)

(58) Field of Classification Search
CPC ........ A61F 2/18; A61F 2/0059; A61F 11/004; A61F 2210/0014; A61F 2230/0013;
(Continued)

(56) References Cited

U.S. PATENT DOCUMENTS 3,897,786 A * 8/1975 Garnett ................. A61F 2/0095
206/370
2008/0262505 A1* 10/2008 Shahoian .............. A61F 11/002
606/108

(Continued)

FOREIGN PATENT DOCUMENTS

EP          2033586 A2    6/2008
JP          2006122094    5/2006
(Continued)

OTHER PUBLICATIONS

Patent Cooperation Treaty, Notification of Transmittal of the International Search Report & the Written Opinion of the International Searching Authority, or the Declaration, PCT/GB2015/050356, dated Apr. 29, 2015, pp. 11.

*Primary Examiner* — Jennifer Dieterle
*Assistant Examiner* — Rebecca Lynee Zimmerman
(74) *Attorney, Agent, or Firm* — Matthew O. Brady

(57) ABSTRACT

The present invention provides a surgical introducer (10) for inserting an implant (22) into a human ear, the introducer comprising a handle (12), a slider (14) movable relative to the handle between a first position and a second position, a retaining means being at least partially defined by the slider, and a releasable locking mechanism biased to lock the slider in said first or second position, wherein, when the slider is in said first position an implant is engaged by the retaining means and when the slider is moved towards said second position the implant is deployed.

5 Claims, 2 Drawing Sheets

(51) Int. Cl.
  *A61B 17/34*   (2006.01)
  *A61F 11/00*   (2006.01)
  A61B 90/00   (2016.01)
  A61B 17/00   (2006.01)

(52) U.S. Cl.
  CPC ... *A61F 11/004* (2013.01); *A61B 2017/00438* (2013.01); *A61B 2090/062* (2016.02); *A61F 2002/183* (2013.01); *A61F 2210/0014* (2013.01); *A61F 2230/0013* (2013.01)

(58) Field of Classification Search
  CPC ........... A61F 2002/183; A61B 17/3468; A61B 2017/00438; A61B 2090/062
  See application file for complete search history.

(56) References Cited

U.S. PATENT DOCUMENTS

| | | |
|---|---|---|
| 2008/0287957 A1 | 11/2008 | Hester et al. |
| 2008/0314961 A1 | 12/2008 | Boundreaux |

FOREIGN PATENT DOCUMENTS

| | | | |
|---|---|---|---|
| RU | 2053736 C1 | 2/1996 | |
| WO | WO9819605 A1 | 5/1998 | |
| WO | WO2006012630 A2 | 2/2006 | |
| WO | WO 2007023296 A1 * | 3/2007 | ......... A61B 17/3468 |
| WO | WO2007023296 A1 | 3/2007 | |
| WO | WO2010031902 A1 | 3/2010 | |
| WO | WO 2012136950 A1 * | 10/2012 | ............... A61F 2/18 |
| WO | WO2012136950 A1 | 10/2012 | |

* cited by examiner

SURGICAL INTRODUCER

FIELD OF THE INVENTION

The present invention relates to a surgical introducer for inserting an implant into the cartilage of a human ear.

BACKGROUND OF THE INVENTION

Prominent ear deformity is common amongst the human population. An ear which projects more than 20 mm from the side of the head is increasingly perceived as prominent as this distance increases. By this estimate, up to 10% of the population may be affected. It is desirable to correct the prominence very early in life when the cartilage is soft and pliable. However, often the prominence is ignored and not treated. Consequently, many children suffer the psychological consequences associated with prominent ears. These consequences can persist into adulthood.

The ear cartilage is cup-shaped and is formed of the conchal fossa and the antihelical fold which allows the ear to lie flat against the side of the head. Prominence may be the result of abnormal formation of the antihelical fold. Alternatively, it may be the result of a deep conchal fossa. One or both of these abnormalities may need to be addressed when correcting prominence of the ear. However, even for ears with a deep conchal bowl, accentuation of the antihelical fold will make a difference to the perception of prominence. In most cases the prominence is apparent at birth.

International patent application number PCT/GB2012/000282 discloses an implant formed of shape-memory material in the shape of a horseshoe for reshaping the cartilaginous portion of an ear. The implant is flattened and loaded into an introducer which assists with insertion of the implant into the ear. When the implant is in the desired position it is deployed to reshape the cartilaginous portion of the ear because it reverts to its horseshoe shape when released from the introducer.

The implant is inserted into the ear using an introducer which holds the implant in its first configuration, and upon insertion the implant adopts its second pre-programmed configuration. The introducer comprises a handle and a slider movable relative to the handle.

The present invention seeks to provide improvements over the introducer disclosed in PCT/GB2012/000282.

SUMMARY OF THE INVENTION

The present invention provides a surgical introducer for inserting an implant into a human ear, the introducer comprising a handle, a slider movable relative to the handle between a first position and a second position, a retaining means being at least partially defined by the slider, and a releasable locking mechanism biased to lock the slider in said first or second position, wherein, when the slider is in said first position an implant is engaged by the retaining means and when the slider is moved towards said second position the implant is deployed.

During surgery, precise control over deployment of the implant is critical to the resulting adjustment to prominence of an ear. If deployment were to occur inadvertently in the wrong position the patient's ear would not take the desired shape. The implant would then need to be removed and further implant inserted. Provision of a locking mechanism means that deployment can only occur upon the conscious decision of a surgeon to extend the slider into a second position The retaining means may be further defined by the handle.

The handle may comprise a body and a slider support member.

The body of the handle may comprise a channel to receive the slider support member and the slider.

The channel may comprise a locking formation having a first locking position and a second locking position according to the first position and second position of the slider respectively.

Provision of a locking formation limits longitudinal movement of the slider to between two fixed positions. This provides certainty to a surgeon that the implant is securely retained by the introducer when the slider is in a first position and that the implant will be deployed when the slider is moved to a second position.

The locking mechanism may comprise a resilient spring engageable with the locking formation of the handle.

Use of a resilient spring biases the locking mechanism in the locked position. The slider cannot be extended, and the implant deployed, without a conscious decision by the surgeon to overcome the spring in order to extend the slider.

The locking mechanism and the slider may be formed from a unitary component.

Forming the slider and resilient spring from a unitary component simplifies the construction of the introducer and minimises manufacturing costs.

The resilient spring may comprise a first portion having a first width received by the channel and a second portion having a second width, greater than the first width engageable with the locking formation of the channel.

The slider may further comprise a visual indicator to assist an operator in identifying when the introducer has been inserted a sufficient distance into the ear of a patient.

Provision of a visual indicator provides the surgeon with a visual aid to identify when the introducer has been inserted the correct distance into the patients ear before deployment of the implant.

The handle may comprise two openings therethrough to each receive a finger of an operator and/or a trigger position to receive a user's index finger.

Given the delicate nature of surgery on a human ear, ergonomic design of the introducer is desirable for the surgeon to have sufficient control over the introducer.

FIGURES

Specific embodiments of the present invention will now be described, by way of example only, with reference to the accompanying drawings in which.

DETAILED SUMMARY OF THE INVENTION

Figure 1:
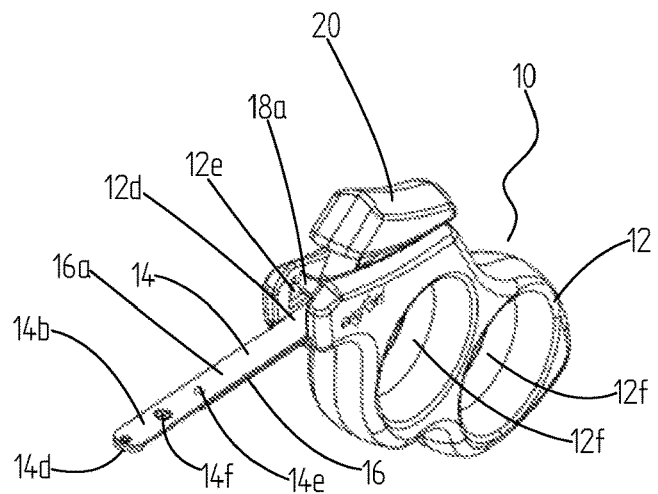
FIG. 1 shows an isometric view of a surgical introducer according to embodiments of the invention.
Figure 2:
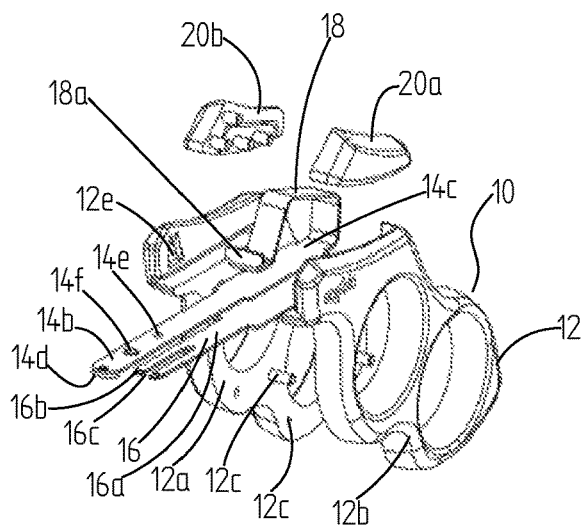
FIG. 2 shows an exploded view of the surgical introducer of FIG. 1.
Figure 3:
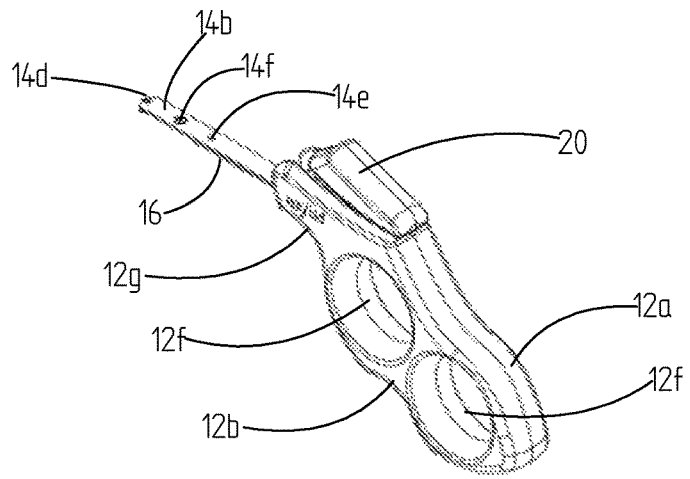
FIG. 3 shows a further view of the surgical introducer of FIG. 1.

FIGS. 1 to 3 show a surgical introducer 10 for inserting an implant, 22 into the cartilaginous portion of a human ear. The introducer 10 comprises a handle 12 and a slider 14 which is movable relative to the handle 12.

The handle 12 comprises a body formed from two mirrored parts 12a, 12b and a slider support 16 extending forwardly of the body 12a, 12b. Each part of the body 12a, 12b includes snap fit connections 12c for joining the two parts of the body 12a, 12b of the handle 12 together. The two parts of the body 12a, 12b define between them a channel 12d within which the slider 14 and slider support 16 are received.

The body 12a, 12b has two apertures 12f therethrough which are configured to each receive an operator's finger. The body also has a trigger grip position 12g to provide flexibility in how the introducer 10 is held.

The slider support 16 comprises a flat plate 14a which is fixed to the body 12a, 12b of the handle 12. The forward end 16b of the slider support 16 is provided with a longitudinal cut-out 16c for receiving a part of the slider 14 to prevent lateral movement of the slider 14 relative to the handle 12.

The slider 14 comprises a substantially flat plate 14a having a distal end 14b and a proximal end 14c. A resilient spring 18 forms an integral part of the slider 14 at its proximal end 14c. The resilient spring is a profiled sprung plate which extends upwardly from the proximal end 14c of the slider 14 and towards the distal end 14b of the slider 14. A portion 18a of the extreme end of the resilient spring 18 is of a greater width than the remainder of the resilient spring 18 and the slider 14.

The distal end 14b of the slider 14 defines a retaining lip 14d which partially retains one end of an implant 22. The retaining lip 14d can be up to 0.6 mm long but will typically be between 0.45-0.5 mm long. The lip can be up to 0.5 mm thick but will typically be between 0.25-0.3 mm thick. The distal end 16a of the slider support defines a similar retaining lip (not shown) of substantially similar dimension which partially retains the opposite end of an implant 22.

A pin 14e is spot welded to the slider 14 for engagement with the longitudinal cut-out 16b of the slider support 16. An embossment 14f is provided between the retaining lip 14d and pin 14e of the slider to provide visual indication of when the introducer 10 is in the desired position. In the illustrated example, the embossment 14f is disposed centrally between the retaining lip 14d and pin 14e of the slider.

The slider 14 is received by the channel 12d of the body 12a, 12b and overlays the slider support 16. The slider 14 can move between a first, extended position and a second, retracted position. The range of longitudinal movement of the slider 14 is inhibited by engagement of the wider portion 18a of the resilient spring 18 with respective indents 12e formed in each part of the body 12a, 12b of the handle 12.

The indents 12e formed in each part of the body 12a, 12b are generally M shaped. The wider portion of the resilient spring 18 has a width corresponding to the maximum distance between the indent 12e of each part of the body 12a, 12b. The range of movement of the slider 14 is thus limited to being equivalent to the distance between the two internal apex of the M-shaped indents 12e.

A cover 20 overlays the resilient spring 18 to provide comfort and a tactile response to a surgeon. The cover 20 is formed from two mirrored parts 20a, 20b which are snap-fitted together around the resilient spring 18.

Figure 4:
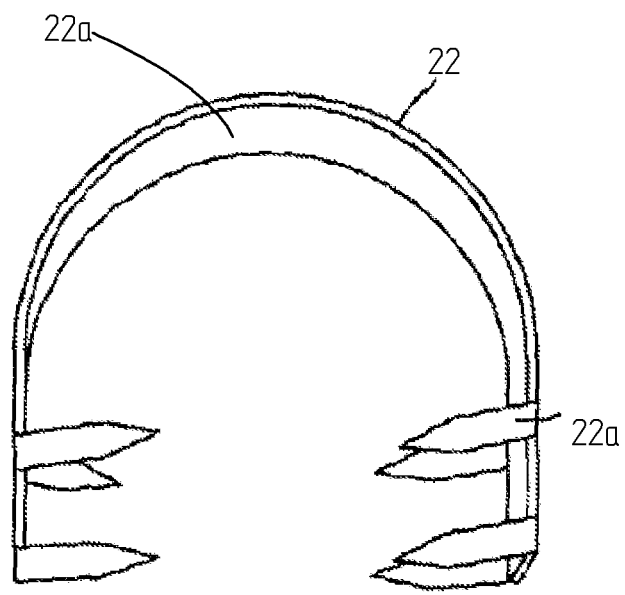
FIGS. 4 and 5 show an implant as used with the introducer of the present invention.
Figure 5:
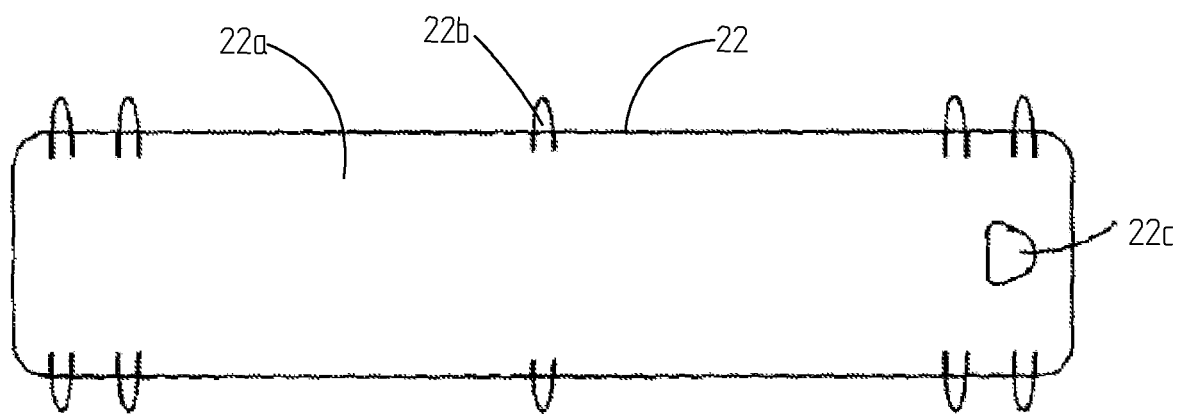

The implant 22, as shown in FIGS. 4 and 5, comprises a nitinol plate 22a which is coated with 24 carat gold. A plurality of tines 22b extend from one side of the plate 22a for engaging with the cartilage of a human ear. The plate 22a includes an opening 22c therethrough to assist with removal of the implant 22 from a human ear once prominent ear deformity has been corrected.

The implant 22, as shown in FIG. 4, is biased in a horse shoe shape in its second pre-programmed configuration. When the implant 22 is loaded into the introducer 10 it is flattened (see FIG. 5) such that it is flattened and retained between the retaining lip 14d of the slider 14 and the retaining lip of the slider support. The slider 14 is in the retracted position when an implant 22 has been loaded into the retaining means. The implant 22 reverts to its biased horseshoe shape when the slider 14 is moved to the extended position and the implant 22 is thus deployed from the introducer 10.

Before the implant 22 can be implanted into an ear of a patient, the patient needs to be given a local anaesthetic so that an incision can be made through the skin of the ear. The skin is then lifted away from the cartilage to create a tunnel. The slider 14 of the introducer 10 is inserted into the tunnel to position the implant 22 in the desired position. The slider 14 is then extended to increase the distance between the distal end 14b of the slider 14 and the distal end 16a of the slider support 16. The implant 22 is then deployed from the introducer 10 and reverts to its natural horseshoe shape around the cartilage of the ear. This has the effect of enhancing the natural shape of the antihelical fold and reducing prominence of the ear.

The above description is given by way of example only and is not intended to limit the scope of the invention.

The invention claimed is:

1. A surgical introducer for inserting a medical implant into a human ear to correct prominent ear deformity, the surgical introducer comprising:
  a handle;
  a slider movable relative to the handle between a first position and a second position; a retaining lips, and a releasable locking mechanism preventing a surgeon from inadvertently deploying the a medical implant without making a deliberate physical action to overcome a spring strength of a resilient member that is biased to lock the slider in said first or second position, wherein, when the slider is in said first position, the medical implant is engaged by the retaining lips and when the slider is moved towards said second position the implant is configured to be deployed into the human ear, wherein the handle comprises a body and a slider support member and the body of the handle comprises a channel to house the slider support member and receive the slider, the channel comprises a locking formation having a first locking position and a second locking position each corresponding to the first position and second position of the slider, respectively, the locking mechanism comprises a resilient spring engageable with the locking formation of the handle via indents formed within the body of the handle, the locking mechanism and slider are a unitary component, and the resilient spring comprises a first portion having a first width received by the channel and a second portion having a second width that is greater than the first width and engageable with the locking formation of the channel.

2. The surgical introducer for inserting an implant into a human ear according to claim 1, wherein the slider further comprises a visual indicator configured to assist an operator in identifying when the introducer has been inserted a sufficient distance into the ear.

3. The surgical introducer for inserting an implant into a human ear according to claim 2, wherein the visual indicator is an embossment.

4. The surgical introducer for inserting an implant into a human ear according to claim 1, wherein the handle comprises two openings therethrough configured to each receive a finger of an operator.

5. The surgical introducer according to claim 1, in combination with an implant formed of shape-memory material and having a first configuration when retained by the retaining lips and a second pre-programmed configuration when configured to be deployed into a patient's ear.

* * * * *